US007988622B2

(12) United States Patent
Achas Gandarias

(10) Patent No.: US 7,988,622 B2
(45) Date of Patent: Aug. 2, 2011

(54) LUMINOUS OPTICAL LARYNGOSCOPE

(75) Inventor: Pedro Achas Gandarias, Getxo (ES)

(73) Assignees: Page 65, S.L., Getxo (ES); S.C.B., S.A., Bilbao (ES)

( * ) Notice: Subject to any disclaimer, the term of this patent is extended or adjusted under 35 U.S.C. 154(b) by 469 days.

(21) Appl. No.: 12/160,741

(22) PCT Filed: Jan. 24, 2006

(86) PCT No.: PCT/ES2006/000025
§ 371 (c)(1),
(2), (4) Date: Oct. 31, 2008

(87) PCT Pub. No.: WO2007/085664
PCT Pub. Date: Aug. 2, 2007

(65) Prior Publication Data
US 2010/0168521 A1 Jul. 1, 2010

(51) Int. Cl.
*A61B 1/00* (2006.01)

(52) U.S. Cl. .................................................. 600/188

(58) Field of Classification Search .................. 600/169, 600/176, 185, 188, 189, 197, 199, 245, 246
See application file for complete search history.

(56) References Cited

U.S. PATENT DOCUMENTS

| 4,076,018 | A | 2/1978 | Heckele |
| 5,647,840 | A * | 7/1997 | D'Amelio et al. ............ 600/169 |
| 5,845,634 | A | 12/1998 | Parker |
| 6,319,195 | B1 | 11/2001 | Nakaichi et al. |
| 2003/0168059 | A1 | 9/2003 | Pacey |

OTHER PUBLICATIONS

International Search Report for PCT/Es 2006/000025 May 26, 2006.

* cited by examiner

*Primary Examiner* — Eduardo C Robert
*Assistant Examiner* — David Comstock
(74) *Attorney, Agent, or Firm* — Nixon Peabody LLP; Jeffrey L. Costellia

(57) ABSTRACT

The invention relates to a luminous optical laryngoscope having a heating device built into the end that is inserted into the patient or the distal end thereof in order to prevent the formation of condensation and to facilitate viewing inside the patient through the laryngoscope.

28 Claims, 9 Drawing Sheets

LUMINOUS OPTICAL LARYNGOSCOPE

FIELD OF THE ART

The present invention relates to a luminous optical laryngoscope having a heating device incorporated at the end inserted into the patient or the distal end of the laryngoscope to prevent steam and to thus allow clearly observing the inside of the patient through the laryngoscope.

PRIOR STATE OF THE ART

Preventing condensation in the medical instruments intended to be inserted into the human body through the respiratory passages is a known problem which has long been attempted to be solved in the state of the art, there being up until now different methods and devices intending to solve this problem.

The main problems are that when an instrument is inserted into the human body through a respiratory passage, mouth or nose, and due to the temperature difference existing between the instrument at room temperature and the inside of the human body, as well as due to the expiration pressure of the air of the lungs in the breathing of the patient, the viewing lens or window located at the end of the inserted instrument becomes misted due to the steam generated, making it impossible or very difficult for the doctor to observe the inside of the patient. In other words, when an element at room temperature is inserted inside the human body, it is necessary to solve the problems caused by pressurized air, hot air and air oversaturated with water.

When the device at room temperature is inserted into the human body, approximately at 20° C., and the temperature of the human body being approximately 36° C., the hot air oversaturated with water of the human body decreases its temperature when it comes into contact with the device, causing the condensation of the air oversaturated with water on the surfaces of the device inserted into the human body and which is at a lower temperature. When the temperature of the hot air decreases, the amount of water in suspension admitted by this cooled air also decreases, the water therefore condensing on the surface of the device which is at a lower temperature than the air inside the human body.

To prevent the previous problems it is necessary to eliminate the temperature difference existing between the lens of the inserted end and the inside of the human body, all of which is carried out by heating said end.

Processes are known in the state of the art for heating the end of the device inserted into the human body by liquid methods (hot saline), therefore when the distal end of the device is inserted, the latter is heated and prevents steam. Other methods consist of using hydrophobic liquids, which repel steam, or also plastic sheets adhering to the distal face of the lens which is inserted into the body. The main problem of these systems is that if once the device is heated and the insertion thereof in the patient has started, it is necessary to remove it again for any reason, for example, it becomes stained, the device cools again, it being again necessary to re-heat it. Likewise, these devices do not work correctly when there is a high water concentration.

The methods powered by an external electric source include the use of cables surrounding the viewing lens or which are incorporated in the frame and located at the end of the viewing instrument. As has been mentioned, said cables are powered by a source outside the viewing instrument and allow heating the lens such that when such lens is inserted inside the human body, there is no temperature difference between both and the formation of steam on the surface of the lens in contact with the inside of the body is prevented.

In these types of devices using cable for transmitting heat to the lens, the diffusion of said heat in the lens depends to a great extent on the diameter of the cable, a larger diameter of the cable being necessary for a better diffusion of heat through the lens and to achieve a larger contact surface between the cable and the lens. Said increase of diameter generates an increase of the instrument to be inserted into the human body as well as an increase of the electric energy necessary to raise the temperature of the lens to the temperature of the human body, an increase of the required power of the power supply source therefore being necessary. The use of cable to raise the temperature of the lens causes the loss of heat between the separations existing between the cable and the lens, and also causes the impossibility of finding a method for achieving the correct tightness with the rear part of said lens, thus allowing the formation of steam on the faces of possible rear elements due to the expiration pressure of the air of the lungs or allowing the introduction of secretions inside the conduit. Another problem associated to the cables is the radial diffusion of the heat, which requires an insulation of its entire periphery to prevent burns of the device which could affect the patient. Likewise the arrangement of the cable in the lens is a complicated process making the end product expensive due to the fact that they have an arrangement in coils or windings, a suitable diffusion of the heat in the lens furthermore not being achieved.

DESCRIPTION OF THE INVENTION

The present invention relates to a laryngoscope with an incorporated heating device, the laryngoscope being of the type formed by a longitudinal body with a first straight section and a curved section after the previous section with a proximal end coinciding with the free end of the first straight section and a distal end at the opposite end of the proximal end. Said body can be internally divided into two independent conduits separated by a central partition. If the body only has one conduit, it will be a viewing conduit for nasotracheal intubation. In the event that said body is formed by two conduits, the first conduit is used for viewing the inside of the patient and the second conduit is used for inserting an endotracheal tube, both conduits being limited in their entire extension by an upper surface and a lower surface. The viewing conduit internally has a certain number of lens or prisms and two image-reflecting surfaces which allow transmitting the image from the distal end of the laryngoscope, inserted into the patient, to the proximal end where the person who is inserting the laryngoscope into the patient is located.

One object of the present invention is to provide a heating device for the type of laryngoscope described which prevents the formation of steam on the faces of the lenses of the viewing conduit when the laryngoscope is inserted into the patient due to the problems of the expiration pressure of the air of the lungs which is furthermore oversaturated with water and at a higher temperature than the device inserted into the human body, in this case the laryngoscope.

To achieve the above, at the distal end of the viewing conduit the laryngoscope has a lens to which there is adhered a flexible planar plastic sheet having adhered thereto a resistance which is in turn planar and flexible which in the face of joining to the lens preferably has a heat conductor adhesive, and a temperature sensor adjacent to said resistance, both elements preferably being independently connected to an electronic temperature control device and said elements being powered by at least one battery incorporated at the proximal end of the laryngoscope.

The objective of the entire assembly described is to maintain the distal lens at the same temperature as the inside of the body of the patient, and to that end the sensor measures the temperature of the lens, said sensor being controlled by a temperature control device, specifically an integrated electronic circuit, switching the power supply to the resistance and allowing to maintain at all times the temperature of the lens at the same temperature as that of the human body, usually between 37 and 42 degrees centigrade. Said electronic circuit is located at the proximal end of the laryngoscope, next to the electric power supply source of the laryngoscope, and is preferably electrically connected to the sensor and to the resistance independently. Other functions of said electronic circuit are:
- continuously rechecking the electronic temperature and lighting control system,
- deactivating the circuit in the event of error in the operation of any of the components of the electric system,
- indicating that the temperature of the lens has reached the determined temperature by means of the lighting element, specifically making the latter blink until reaching said temperature and stop blinking when it reaches such temperature,
- maintaining the voltage of the lighting point constant and,
- deactivating the system when the battery or batteries have almost been used up.

Likewise, to prevent hot air from being introduced in the viewing conduit due to the expiration pressure of the lungs of the patient, which drives said hot air against the distal face of the lens at a certain pressure and could form steam in the rest of the optics of the laryngoscope when the hot air passes to the rear lenses, as well as to prevent the introduction of other fluids of the inside of the human body in the viewing conduit of the laryngoscope, being able to affect the optics or damage the electric system, a sealing gasket, preferably made of an elastic material, is used, which gasket surrounds the assembly formed by the prism or lens, the heat conductor adhesive, the plastic sheet and the flexible planar resistance adhered to the outside of the prism. Said gasket preferably has at least two ribs, preferably running along three of its four faces and ensuring the tightness and sealing upon creating a tight air chamber between both ribs and the body of the laryngoscope. Thus, not only is the entrance of air into the viewing conduit prevented, but the entrance into said conduit of secretions of the human body such as saliva, fluids, blood, etc. is also prevented. Furthermore, it is possible that the rest of the lenses, in addition to the proximal lens, are heated to this ensure with greater assurances that the steam will not affect the view. An additional function of the gasket is to prevent the heat of the resistance from being transmitted to the frame of the laryngoscope and, by contact, to the patient, i.e., the elastic material of the gasket is preferably heat-insulating.

A second object of the present invention is to achieve that the viewing of the entrance of the trachea by the user of the device is perfectly independent of who uses it. To achieve said perfect viewing of the inside of the patient through the laryngoscope it is necessary for the distance between the eve of the person inserting the laryngoscope and the first proximal lens thereof to be maintained constant.

Likewise, to achieve viewing the trachea from outside a patient, specifically from the mouth, it is necessary to overcome the difference of angles between the oral axis and the laryngeal axis, the difference of axes being approximately between 60° and 120° when the neck is a neutral position. The three axes which are relevant during the insertion of a laryngoscope with the neck in a neutral position are the oral axis, the pharyngeal axis and the laryngeal axis. A laryngoscope which only works with the neck in a neutral position requires, as has been mentioned, having a gain in the angle of vision between the oral axis and the laryngeal axis between 60° and 120°. This is due to the fact that with the neck and the head in a neutral position, the angle formed between the oral axis, the pharyngeal axis and laryngeal axis would be approximately between 60° and 120°. In those approximately 60° and 120°, the axis of vision would be formed by the oral axis, the pharyngeal axis and the laryngeal axis and would be located opposite to the trachea. To overcome this difference of angle between the oral axis and the laryngeal axis in a neutral position, only laryngoscopes achieving this by means of fiber-optic are known in the state of the art.

To make the distance between the eye of the person inserting the laryngoscope and the first proximal lens remain inalterable and to make the axis of entrance to the trachea be aligned with the proximal optical axis of exit of the laryngoscope, there is a viewer which in addition to maintaining the distance between the eye and the lens, facilitates the alignment of the eye with the optical axis imaginarily running along the viewing conduit. Said viewer is preferably made of an elastic material to allow its easy insertion in the proximal end of the laryngoscope as well as to prevent injuring the eye or face of the person inserting the laryngoscope into the patient due to possible collisions against the viewer.

An additional objective of the invention is to achieve a sharp and clear image from the distal end of the laryngoscope (inserted into the patient) to the proximal end thereof (which is maintained outside the patient and the inside of the patient is observed from it). To allow said perfect image transmission, the viewing conduit internally has at least two optical elements of the lens, prism and/or image-reflecting surface type, located such that they allow a perfect image transmission and thus observing the inside of the patient from the viewer. It preferably has an assembly of lenses and/or prisms in combination with two image-reflecting surface, they are combined with a lighting system which lights up the inside of the patient while inserting the laryngoscope. Said lighting device has a lighting element, preferable an LED device, which is located at the distal end next to the distal prism or lens.

Another object of the present laryngoscope is to facilitate the guiding of the endotracheal tube in the exit of the endotracheal conduit (in the case of a device with two conduits). To that end, the distal end of the laryngoscope has a tab facilitating the insertion thereof into the patient and a flange guiding the subsequent insertion of the endotracheal tube inside the patient. Said tab lifts the epiglottis and has a characteristic shape, shifted towards the endotracheal conduit, to lift the tissues which might fall on the endotracheal tube when the latter is being inserted inside the patient and which would prevent the perfect insertion of said tube into the trachea because they can shift the direction of exit thereof when said tissues fall on the endotracheal tube. To achieve a perfect insertion of the endotracheal tube, the device has at its distal end, specifically at the end of the side wall of the endotracheal conduit, a wedge-shaped flange or projection towards the inside of said conduit the objective of which is to direct the end of the endotracheal tube towards the entrance of the trachea as well as to allow observing said end of the tube while it is inserted into the trachea from the distal end through the viewing conduit. A triangle is thus formed such that each of its three vertices is formed by the exit of the axis of vision of the laryngoscope (directed towards the right), the exit of the endotracheal tube of the laryngoscope (directed towards the left) and the entrance to the trachea.

Another object of the device of the present invention is to achieve the recording of the insertion process as well as its emission and transmission to an image device, such as a television or monitor for example. To that end, the mentioned viewer can be substituted with a camera transmitting, by means of wiring or a wireless system, images to a receiver which can be either a digital or an analog receiver. Said camera is coupled, like the viewer, to the proximal end of the laryngoscope.

An additional object of the present invention consists of substituting the optical elements, lenses, prisms and reflecting surfaces with other devices, specifically with Fresnel prisms, which also allow a correct image transmission.

Another object of the present invention is to have a laryngoscope which can be reused. To that end, there is a laryngoscope with two separable parts, a first part corresponding to a first straight section of the proximal area of the laryngoscope and comprising the housing of the battery, the first lens, the microcontroller or integrated electronic circuit, electric conductors and the viewer, and a second part corresponding to a second straight section and the curved section of the laryngoscope to its distal area and comprising the lenses behind the first lens, the planar image-reflecting elements, electric conductors and the lighting device. The coupling between said first part and said second part is carried out by means of flanges arranged in the first part which are housed in grooves arranged in the second part. For the coupling of the electric components, specifically the electric conductors of the first part and of the second part, suitable electrical connection elements, preferably jacks, are used. By means of this arrangement, the proximal part of the laryngoscope, including the elements that are most contaminating and have a higher economic cost, can be reused and substituted with the distal part which mainly houses most of the lenses and the lighting device.

DESCRIPTION OF THE DRAWINGS

For the purpose of facilitating the understanding of the invention, reference is made below to the following figures accompanying the description.

DESCRIPTION OF A PREFERRED EMBODIMENT

Figure 1:
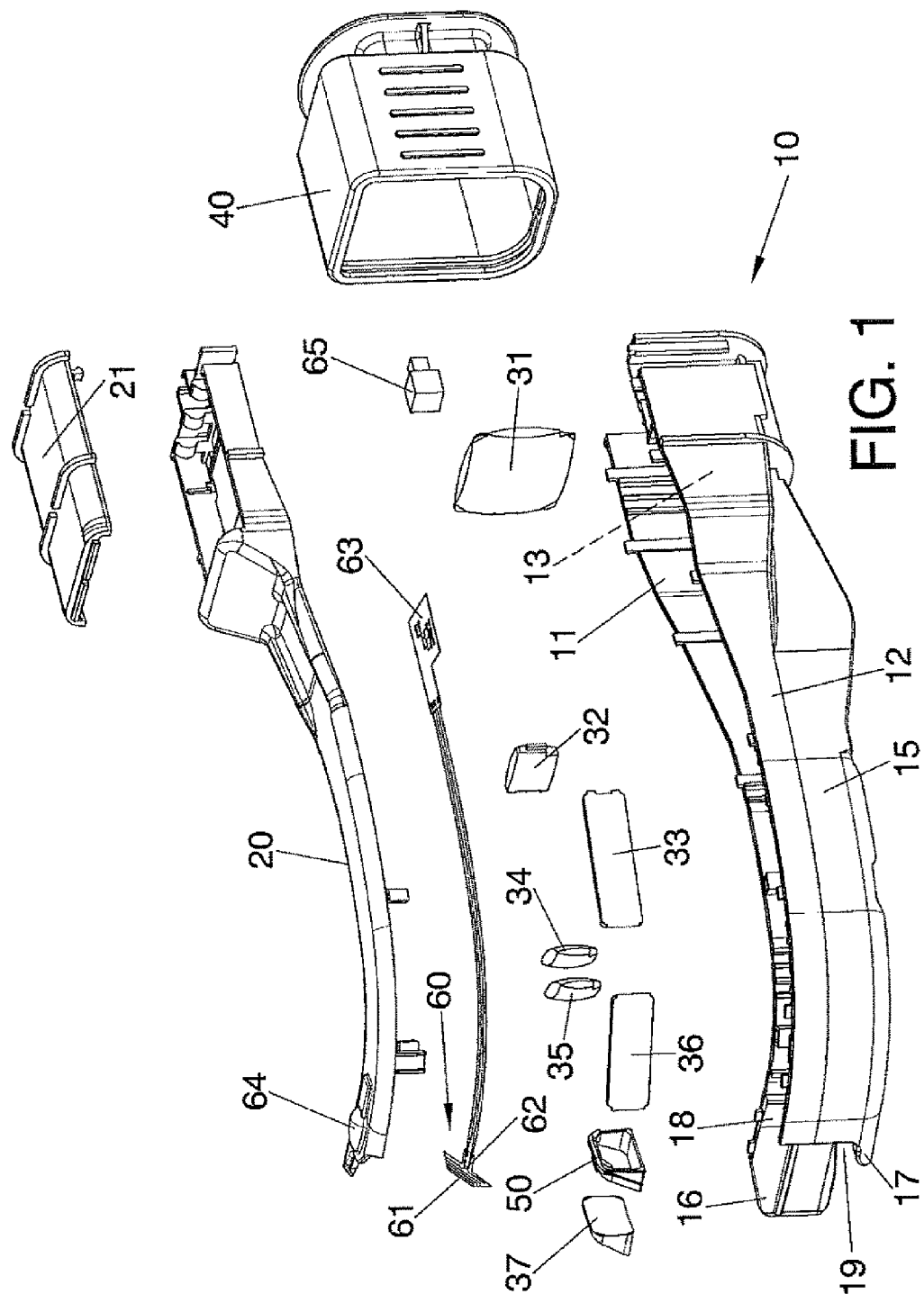
FIG. 1 shows an exploded view of a luminous optical laryngoscope, in which its components are observed before they are assembled.
Figure 2:
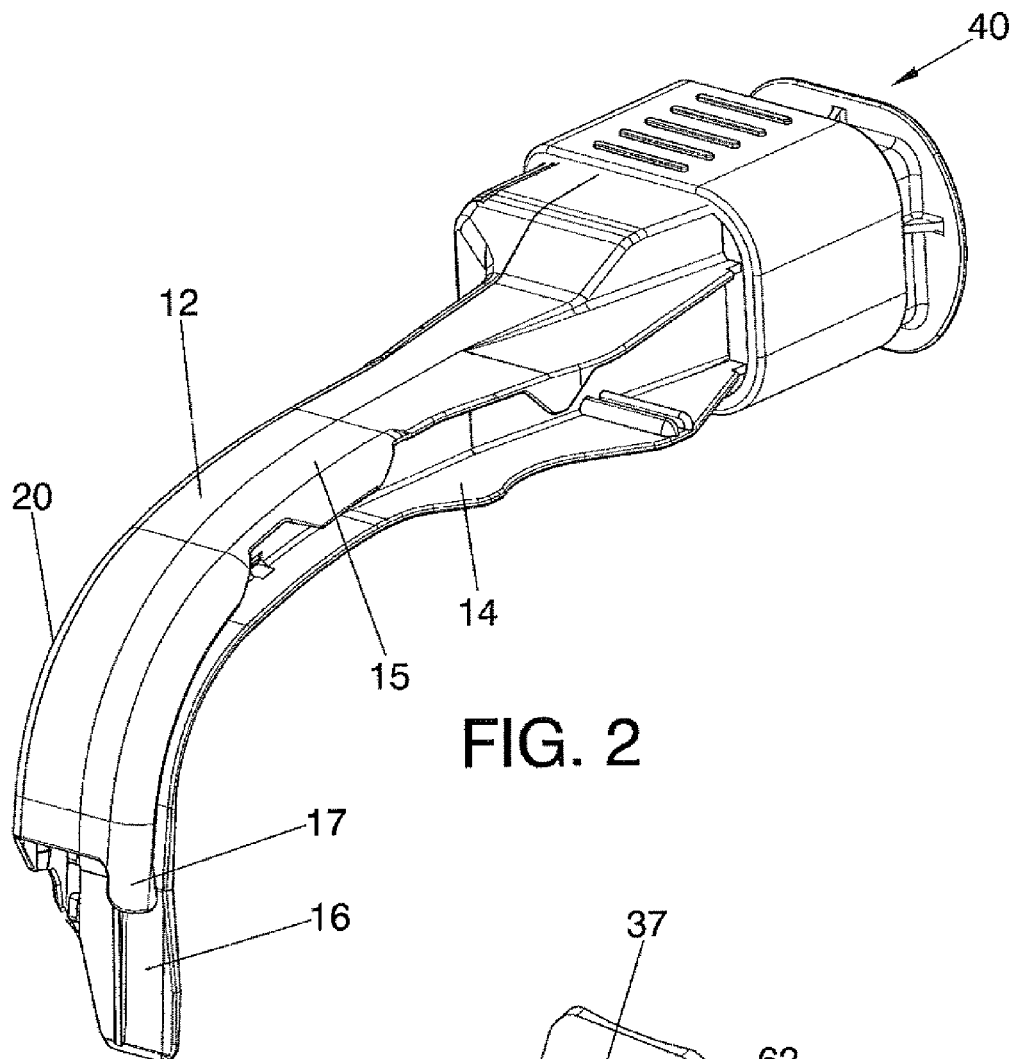
FIG. 2 shows an assembled luminous optical laryngoscope.
Figure 3:
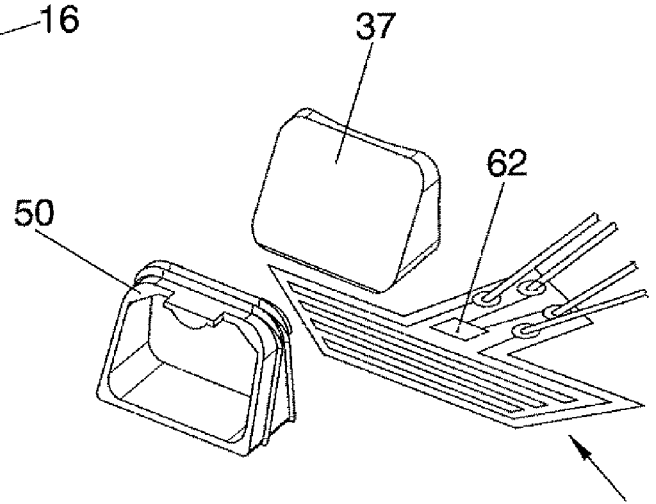
FIG. 3 shows the assembly formed by the lens located at the distal end of the laryngoscope, the resistance and the sealing gasket, before they are assembled.
Figure 4:
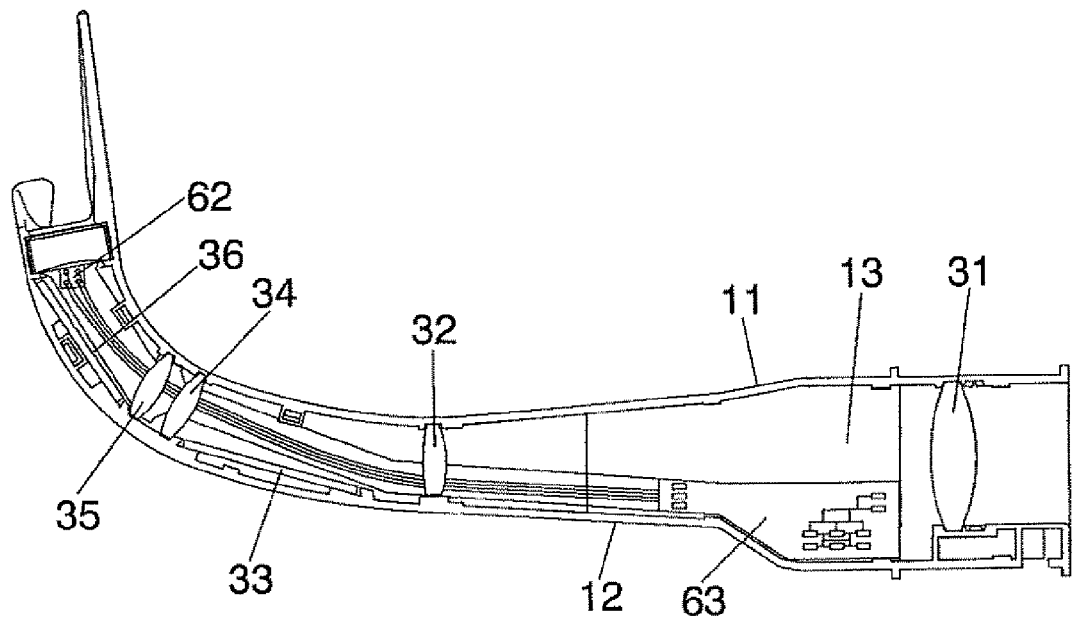
FIG. 4 shows a plan section of the frame of the laryngoscope.
Figure 5:
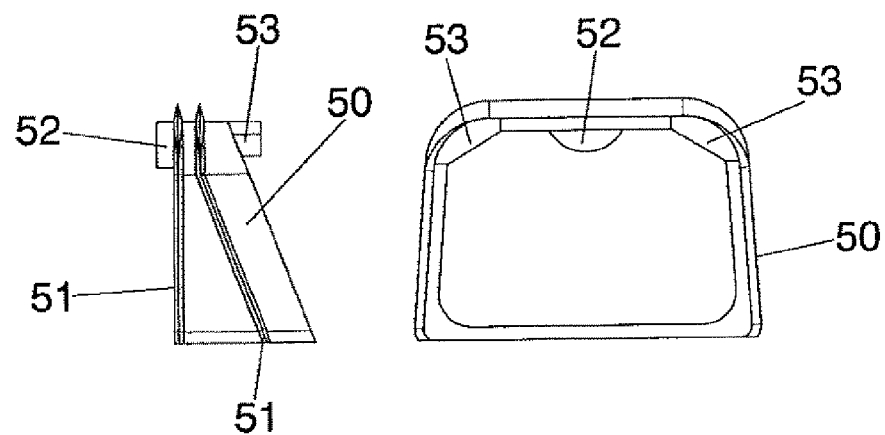
FIG. 5 shows a front and side view of the sealing gasket located in the distal lens.
Figure 6:
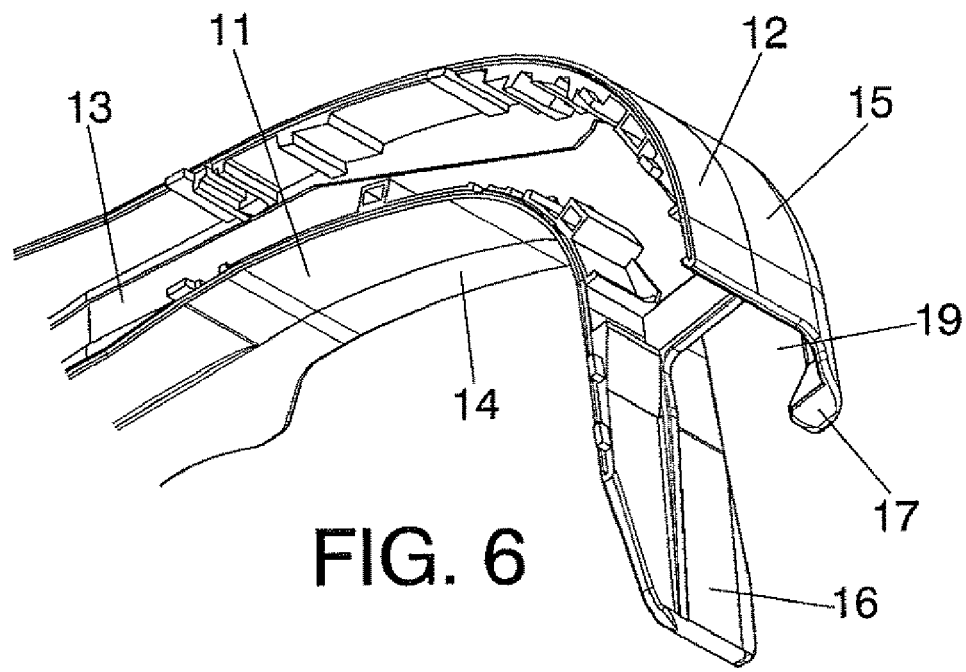
FIG. 6 shows a perspective view of the distal end of the laryngoscope.
Figure 7:
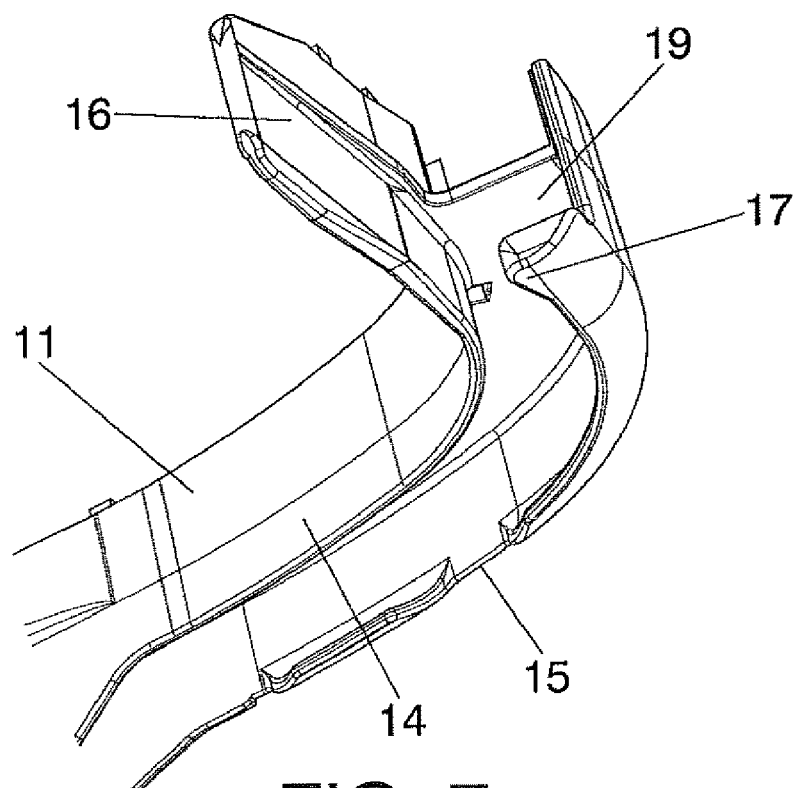
FIG. 7 shows a perspective view of the distal end of the laryngoscope.
Figure 8:
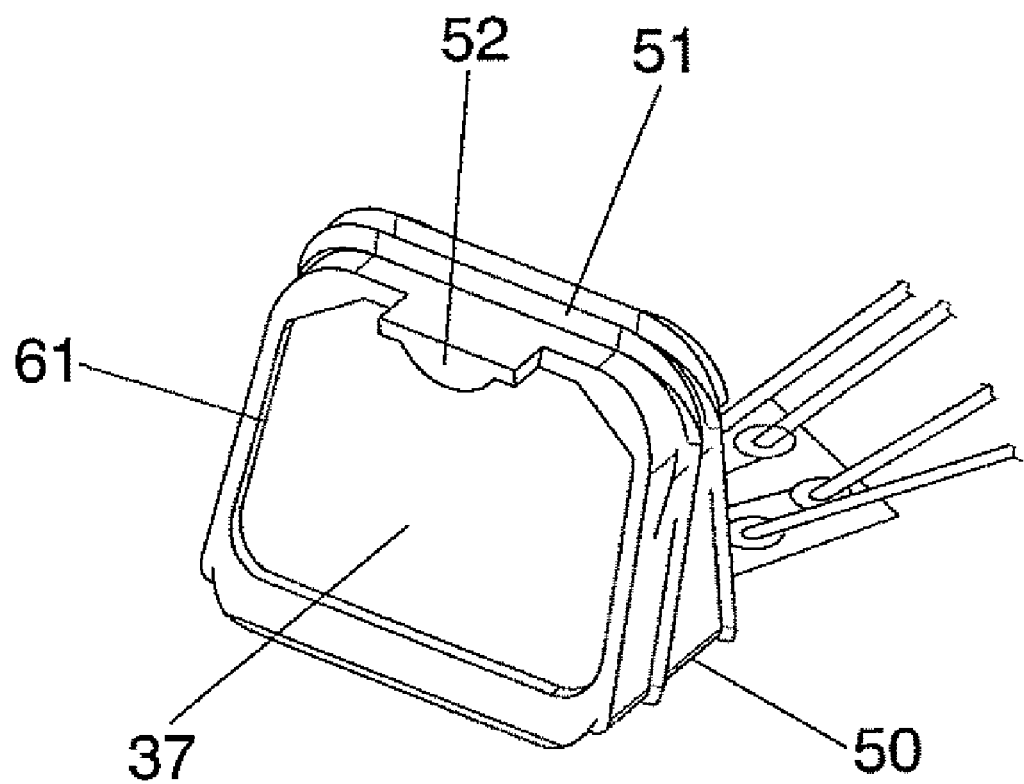
FIG. 8 shows the assembled assembly formed by the distal prism, the resistance and the sealing gasket.
Figure 9:
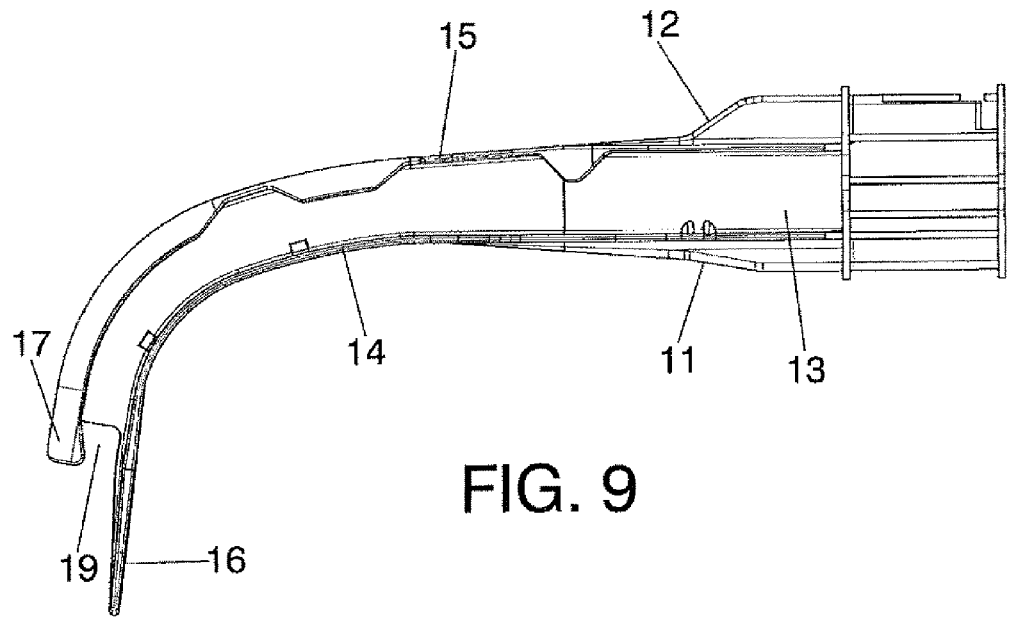
FIG. 9 shows a side wall of the endotracheal conduit.
Figure 10:
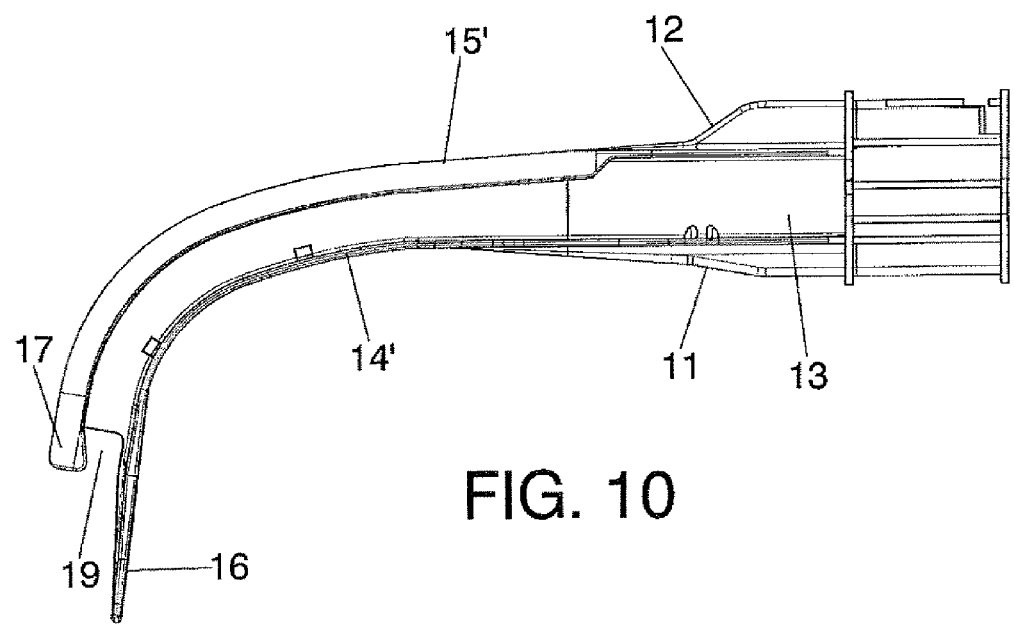
FIG. 10 shows an alternative side wall of the endotracheal conduit.
Figure 11:
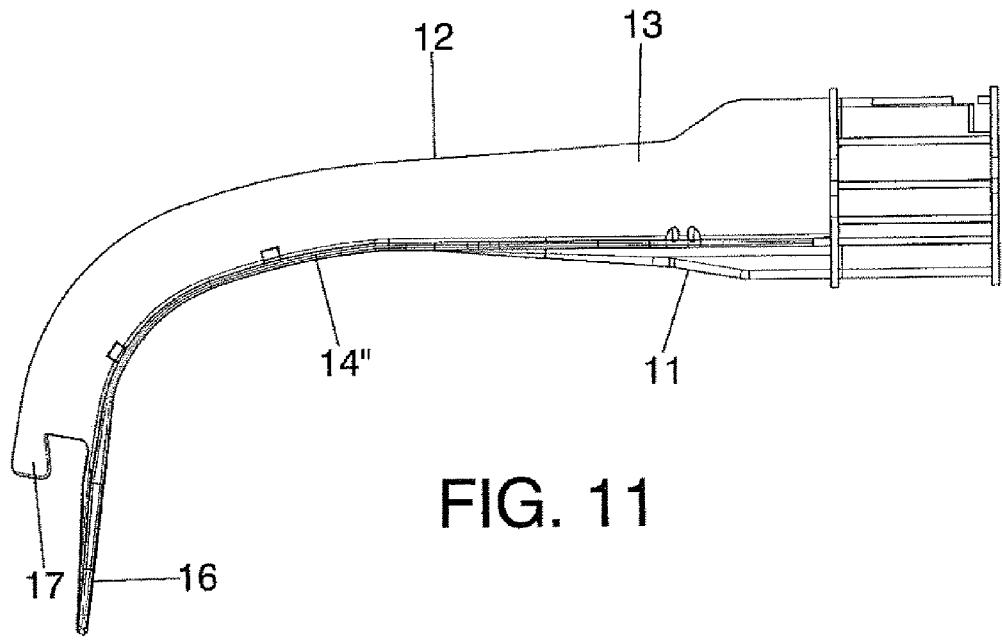
FIG. 11 shows a third alternative of a side wall of the endotracheal conduit.
Figure 12:
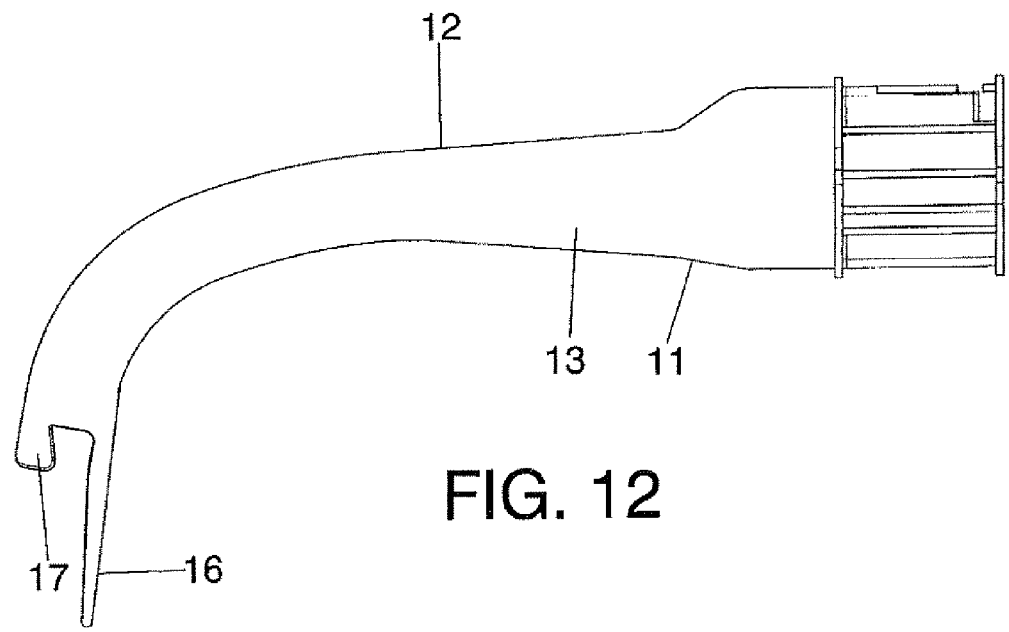
FIG. 12 shows a laryngoscope without an endotracheal conduit.
Figure 13:
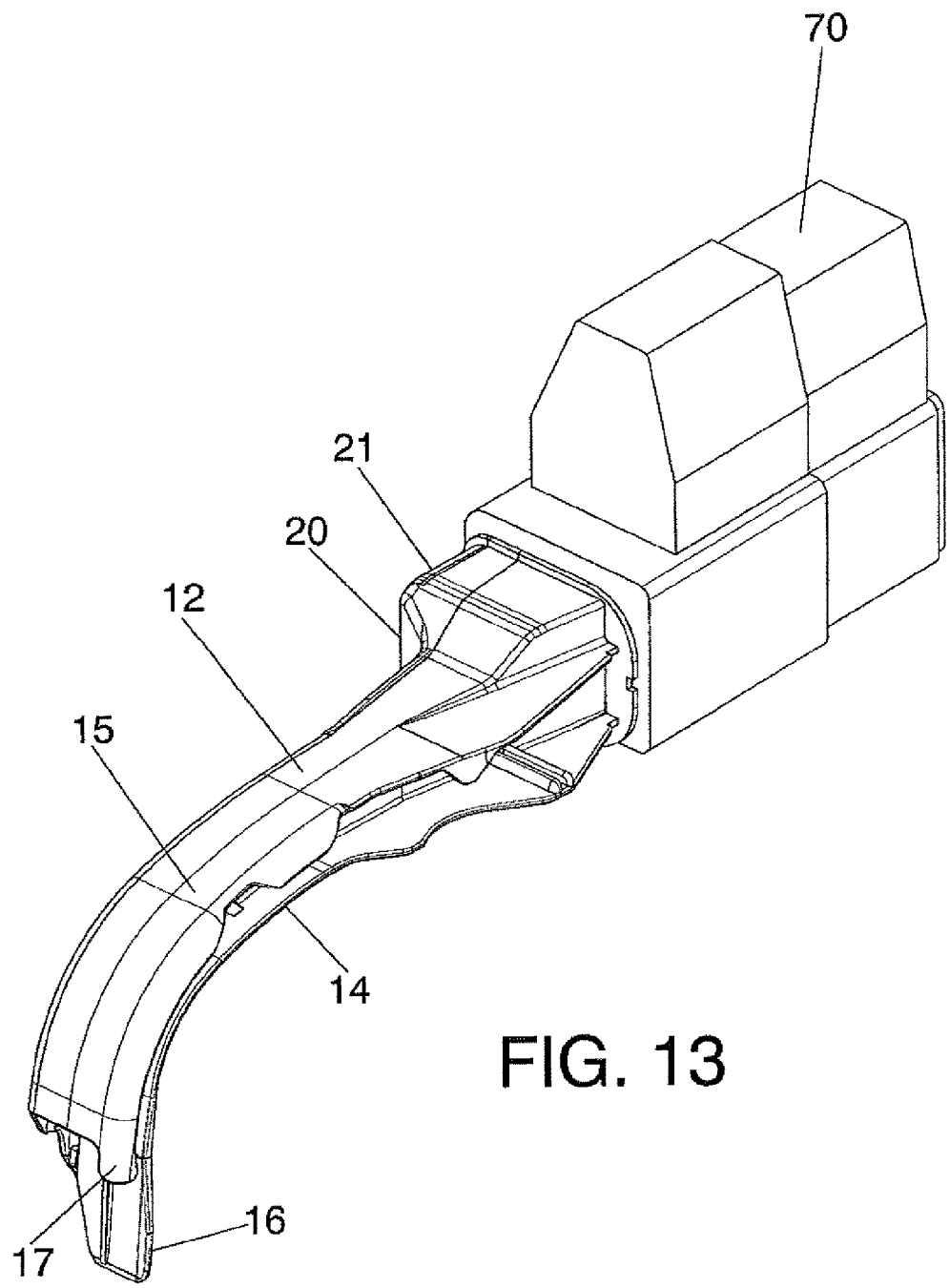
FIG. 13 shows a laryngoscope with an incorporated camera.
Figure 14:
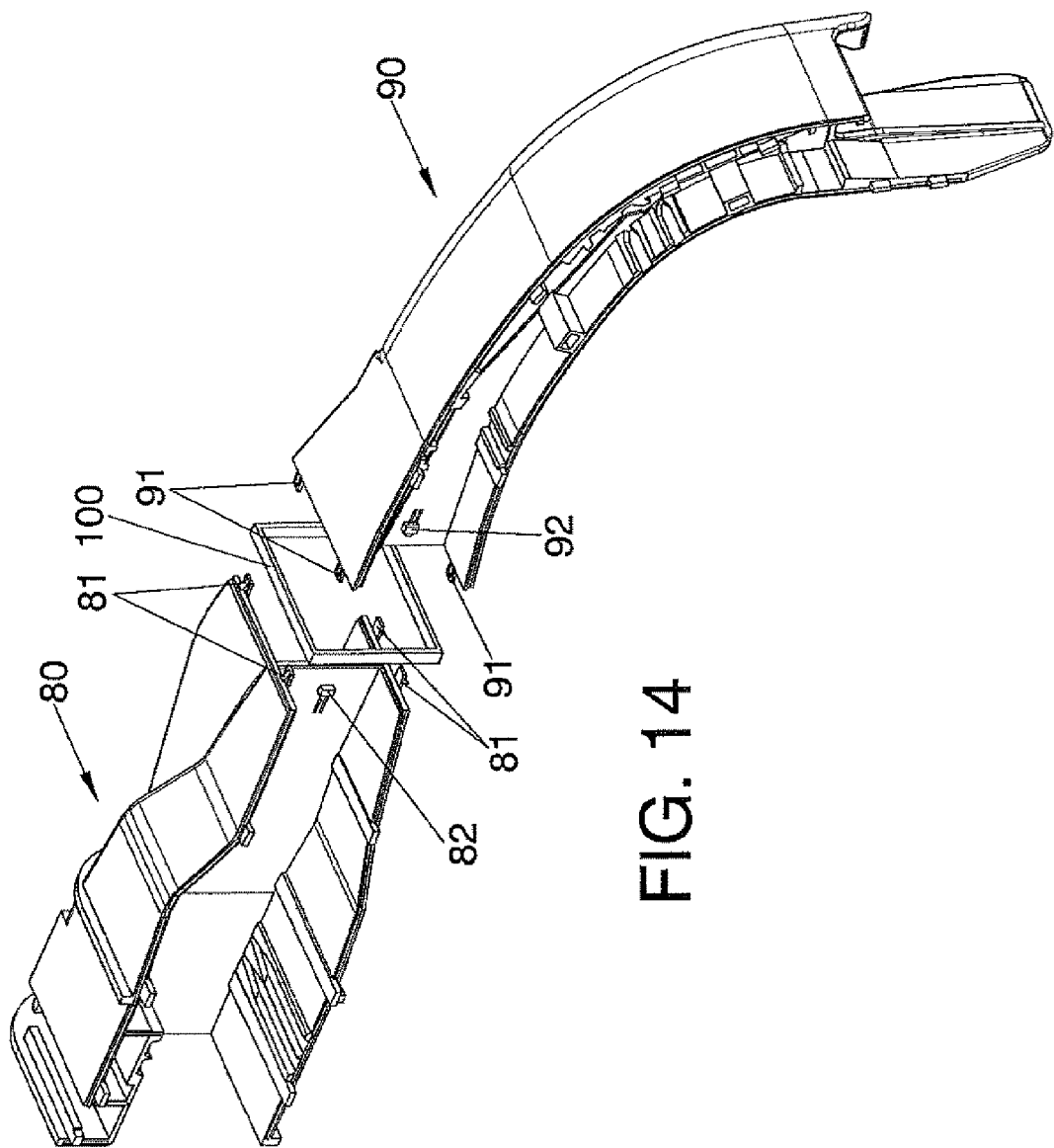
FIG. 14 shows a laryngoscope which can be divided into two parts.

The laryngoscope object of the present invention is of the type formed by a longitudinal body with a first straight section and a curved section after the previous section with a proximal end coinciding with the free end of the first straight section and a distal end at the opposite end of the proximal end, said body being internally divided into two independent conduits separated by a central partition. The first conduit 19 is used for inserting an endotracheal tube and the second conduit 18 is used for viewing the inside of the patient, particularly for viewing the entrance of the trachea where the endotracheal tube must be inserted.

The laryngoscope is formed by a frame 10 including an endotracheal conduit 19 for guiding the endotracheal tube (not shown) and the viewing conduit 18. The latter conduit must be insulated from the outside, therefore it includes a side cover 20 insulating the elements arranged inside the viewing conduit 18 from the outside.

Said frame is divided into the two mentioned conduits, the endotracheal conduit 19 and the viewing conduit 18, by means of a separating partition 13 running along the entire length of the laryngoscope dividing it, as has been mentioned, into to parts. Likewise, the viewing conduit 18 is delimited, apart from by the separating partition 13, by an upper wall 11 and a lower wall 12 and by the mentioned side cover 20.

However, the endotracheal conduit 19 only has an upper wall 14 and a lower wall 15, in addition to the separating partition 13, allowing the insertion of the endotracheal tube along said conduit 19 as well as its separation from the laryngoscope once the intubation has been carried out. To allow the endotracheal tube to slide through the inside of the endotracheal conduit 19 without it "coming out" of such conduit but at the same time allowing the subsequent removal of the tube, said conduit 19 has one or several side walls which do not join the upper wall 14 and the lower wall 15, parallel to the plane containing the separating partition 13 and arranged at certain points of the conduit 19.

In a preferred embodiment, the endotracheal conduit has three side walls separated from one another between the upper wall 14 and the lower wall 15, the first side wall being located at the distal end of the laryngoscope and covering the second straight section of the laryngoscope and the end of the curved section thereof, the second side wall, having a smaller length than the first side wall and being separated from it, is located immediately after the start of the curved section of the laryngoscope, and the third side wall, with a smaller size than the second side wall, is located approximately in the middle of the first straight section of the laryngoscope.

In a second embodiment, the endotracheal conduit has a single side wall between the upper wall 14' and the lower wall 15', which side wall extends approximately from the middle of the first straight section of the laryngoscope to the end of the second straight section thereof.

In a third embodiment, the endotracheal conduit has no lower wall 15, 15' or side wall, it only has an upper wall 14".

To facilitate the guiding of the endotracheal tube at the exit of the endotracheal conduit, the distal end of the laryngoscope has a tab 16 facilitating the insertion of the laryngoscope into the patient as well as the subsequent insertion of the endotracheal tube due to the flange 17. Said tab 16 lifts the epiglottis and has a characteristic shape, shifted towards the endotracheal conduit, to lift the tissues which might fall on the endotracheal tube when the latter is being inserted inside the patient. Said tab 16 acts in combination with the flange or projection 17 towards the inside of the endotracheal conduit, arranged in the side wall thereof and being wedge-shaped, directing the end of the endotracheal tube towards the entrance of the trachea when it comes out of the conduit as well as allowing to observe said end of the tube while it is inserted into the trachea from the distal end through the viewing conduit. A triangle is thus formed the vertices of which are formed by the exit of the axis of vision of the laryngoscope (directed towards the right), the exit of the endotracheal tube of the laryngoscope (directed towards the left) and the entrance to the trachea.

Inside the viewing conduit 18 there are located, in addition to the heating and lighting systems, the different components of the optical system which allow transmitting the image from the distal end of the laryngoscope to the proximal end thereof. Specifically, five lenses 31, 32, 34, 35, 37 and two image-reflecting surfaces, preferably mirrors 33, 36, are arranged, all of them located in proximal to distal order as follows:

- a first lens 31 located at the proximal end of the laryngoscope, at the beginning of the first straight section, the objective of which is to magnify, transmit and focus the reflected image,
- a second lens 32 located approximately at the end of the first straight section, before the start of the curved section and the objective of which is to magnify and transmit the image between the first lens and the first reflecting element,
- a first reflecting element 33 located in the lower wall 12 and at the beginning of the first curved section,
- a third lens 34 located after the first reflecting element 33, the objective of which is to achieve image transmission between the reflecting element 33 and the fourth lens 35,
- a fourth lens 35, after the third lens 34, for the purpose of achieving optimal image transmission between the third lens 34 and the second reflecting element 36,
- a second reflecting element 36, located at the end of the curved section and supported on the same lower wall 12 of the body of the laryngoscope as the first reflecting element 35, and
- a fifth lens 37, with a preferably prismatic shape and a trapezoidal cross-section, located in the second straight section of the laryngoscope, at its distal end, immediately after the end of the curved section thereof and therefore after the second reflecting element 36.

Said optical elements or components can be substituted with one and the same number or with a different number of Fresnel prisms to achieve image transmission in an alternative and different manner.

During the insertion of the laryngoscope through a respiratory passage of the patient and due to the temperature difference existing between the laryngoscope at room temperature and the inside of the human body, as well as due to the expiration pressure of the air of the lungs during the breathing of the patient, the distal face of the fifth lens 37 can become misted due to the steam generated, preventing the correct and sharp view of the entrance of the trachea through the viewing conduit. To prevent the above, a planar and flexible resistance 61, preferably of 15Ω, is arranged, which resistance is preferably formed by a nickel and copper alloy mounted on a planar and flexible plastic sheet, preferably made of polyester, which also preferably surrounds three of the four faces of the side perimeter of said prismatic lens 37. Said resistance 61 and the lens 37 are joined by means of a heat conductor adhesive.

Likewise, and on the material of the resistance 61, there is located a sensor 62, preferably of the NTC (Negative Temperature Coefficient) thermistor type, to control the temperature of the lens and to maintain it constant, preventing harming the patient due to heat. Both elements are independently connected and controlled by a temperature control device 63 located at the proximal end of the laryngoscope, said device being an integrated electronic circuit. By means of the previous device, it is possible to maintain the temperature of the lens preferably between 37 and 42 degrees, which is the usual temperature of the human body, thus preventing the formation of steam on said lens 37.

To prevent the air expelled by the patient from being introduced in the viewing conduit 18 through the gap which might exist between the contours of the fifth lens 37 joined to the resistance 61 and the frame 10, due to the expiration pressure during the breathing of the patient, an elastic gasket 50 into which the fifth lens 37 and the resistance 61 are inserted has been arranged. Said gasket additionally has at least one rib 51 running along at least one part of the perimeter of the gasket. The gasket 50 preferably has two ribs 51 running along three of its four faces, creating a air chamber therebetween in combination with the body of the laryngoscope and which ensures the tightness of the viewing conduit and prevents the entrance of hot air therein, which could mist up the components of the viewing system located after the fifth prismatic lens 37, and also prevents the entrance of secretions or fluids which could affect the view or damage the electric system. Said gasket 50 additionally has a tab 52 perpendicular to the contour of the gasket 50 and which is projected towards the inside thereof. Said tab 52 is located on the side of the gasket 50 which is contact with the cover 20 of the viewing conduit once the cover 20 is mounted on the frame 10. The objective of said tab is to prevent the return light generated by a lighting point arranged in the housing 64 of the cover 20, preferably an LED (Light Emitting Diode), which is located at the distal end of the cover 20 of the viewing conduit to light up the entrance of the trachea and allow viewing said entrance to the trachea from the proximal end of the laryngoscope. Likewise said gasket 50 has, in at least two of its corners, a pair of bevel edges 53 per corner the function of which is to act as supports for the prism 37 which is inserted into the gasket 50.

The previous elements, specifically the resistance 61, the sensor 62, the temperature control device 63 and the lighting point 64, are powered by at least one battery located in a housing arranged in the cover 20 of the viewing conduit 18. Said battery is protected by a lid 21.

The entire electric/electronic system is activated and deactivated by pressing a switch 65 located at the proximal end of the laryngoscope and covered by a viewer 40.

Once all the elements have been incorporated in the viewing conduit 18, the cover 20 of said conduit 18 is joined to the frame or body 10 of the laryngoscope by means of any joining method, preferably heat welding or ultrasound, ensuring the tightness of the viewing conduit 18 and its insulation from the outside of the laryngoscope.

For the correct viewing from the proximal end of the viewing conduit 18 of the entrance to the trachea of the patient, it is necessary for the distance between the eye of the person who inserts the laryngoscope and the first lens 31 to be suitable and to be maintained constant, as well as for the alignment of the optical axis with the eye of the user to be perfect. To that end, there is a viewer 40 which is coupled to the proximal end of the laryngoscope and allows, in addition to maintaining said distance constant, aligning the eye of the person who inserts the laryngoscope with the optical axis of the viewing conduit 18. Said viewer is preferably made of rubber to reduce the risk which possible collisions against the viewer could give rise to. Said viewer 40 is coupled to the proximal end surrounding the four surfaces of the proximal area, including the housing where the battery or batteries and the proximal lens are included.

It is possible to substitute the viewer 40 with a camera 70 capturing the intubation process, thus allowing to carry out the intubation viewing the laryngoscope insertion process through a monitor. To that end, a camera 70 connected to a receiver, preferably in a wireless manner although it can also be by means of wires, is incorporated, which camera transmits the images to such receiver in order to be subsequently suitably processed.

In the laryngoscope object of the present invention, it is necessary for the axis of exit of the vision of the viewing conduit 18 and of exit of the endotracheal conduit 19 to meet at the axis of the entrance of the trachea, to enable constantly viewing the entrance of the trachea and the insertion of the endotracheal tube therein. The following is essential to achieve the above:

The prismatic shape of the fifth lens 37, which changes the direction of the axis of vision, and The distal shape of the endotracheal conduit 19, formed mainly by the projection or wedge 17 shifting the endotracheal tube towards the entrance of the trachea during its insertion.

The laryngoscope can also be divided into two separable parts, a first part corresponding to a first straight section 80 of the proximal area of the laryngoscope and comprising the housing of the battery, the first lens, the microcontroller or integrated electronic circuit, electric conductors and the viewer, and a second part corresponding to a second straight section and the curved section 90 of the laryngoscope to its distal area and comprising the lenses behind the first lens, the reflecting elements, electric conductors and the lighting device. Between both parts 80, 90 there is located a gasket 100 the main objective of which is to prevent the entrance of light in the viewing conduit. The coupling between said first part 80 and said second part 90 is carried out by means of flanges 81 arranged in the first part which are housed in grooves 91 arranged in the second part. For the coupling of the electric components, specifically the electric conductors of the first part 80 and of the second part 90, jacks 82, 92 are used. By means of this arrangement, the proximal part 80 of the laryngoscope, including the elements that are most contaminating and have a higher economic cost, can be reused and substituted with the distal part 90 which mainly houses most of the lenses and the lighting device.

The invention claimed is:

1. A luminous optical laryngoscope comprising a longitudinal body (10) with a first straight section and a curved section after the previous section with a proximal end coinciding with the free end of the first straight section and a distal end at the opposite end of the proximal end, with a lighting device at said proximal end, said body being formed by at least a first conduit (18), used for viewing the inside of the patient, and said viewing conduit having a closed cross-section in its entire length and limited therein by an upper surface (11), a lower surface (12), a side cover (20), a side partition (13) and two optical elements inside it, characterized in that it comprises at least:

One resistance (61) joined to at least one lens or prism (37),
One temperature sensor (62) adjacent to said resistance (61),
One temperature control device (63) connected to at least said resistance (61) and said sensor (62),
One battery powering the above, and
One flexible sealing gasket (50) into which said at least one lens (37) together with said at least one resistance (61) are inserted, said assembly formed by the lens (37) and the resistance (61) being located in the body (10) of the laryngoscope.

2. The laryngoscope according to claim 1, characterized in that the lens or prism (37) is located at the distal end of the viewing conduit (18) of the laryngoscope.

3. The laryngoscope according to claim 1, characterized in that the electric resistance (61) is planar and flexible and is joined to the perimeter of the edge of the lens (37) by means of a heat conductor adhesive.

4. The laryngoscope according to claim 1, characterized in that the electric resistance (61) is formed by a nickel and copper alloy on a polyester base.

5. The laryngoscope according to claim 1, characterized in that said electric resistance (61) has a resistance between 5Ω and 30Ω.

6. The laryngoscope according to claim 1, characterized in that the sensor/thermistor is of the NTC (Negative Temperature Coefficient) type.

7. The laryngoscope according to claim 1, characterized in that the temperature control device (63) is a microcontroller.

8. The laryngoscope according to claim 7, characterized in that said microcontroller (63) is located at the proximal end of the laryngoscope and is connected by means of electric connectors to the resistance (61) and to the temperature sensor (62) adhered to the lens (37) as well as to the lighting device.

9. The laryngoscope according to claim 1, characterized in that said lens (37) is prismatic and has a trapezoidal cross-section.

10. The laryngoscope according to claim 1, characterized in that the sealing gasket (50) has at least one rib (51) on its surface running along at least one part of the perimeter thereof.

11. The laryngoscope according to claim 10, characterized in that the sealing gasket (50) has two ribs (51) separated from one another, creating a tightness chamber between both and in combination with the frame, said ribs (51) running along at least three of the four sides of the gasket (50).

12. The laryngoscope according to claim 1, characterized in that the sealing gasket (50) has a flange (52) perpendicular to the contour of the gasket which is projected towards the inside of said gasket.

13. The laryngoscope according to claim 1, characterized in that the sealing gasket (50) has at least two pairs of bevel edges (51) located in at least two of its corners acting as supports for the lens (37).

14. The laryngoscope according to claim 1, characterized in that it has a housing for the battery located at the proximal end of the laryngoscope connected to a switch also located at said proximal end of the laryngoscope.

15. The laryngoscope according to claim 1, characterized in that at least the optical elements which the viewing conduit (18) internally incorporates are:

a first lens (31) located at the proximal end of the laryngoscope, at the beginning of the first straight section,
a second lens (32) located approximately at the end of the first straight section, before the start of the curved section,
a first reflecting element (33) located at the beginning of the first curved section,
a third lens (34) located after the first reflecting element (33), a fourth lens (35), after the third lens (34), a second reflecting element (36), located at the end of the curved section and supported on the same wall of the body of the laryngoscope as the first reflecting element (33), and a fifth lens (37) with a prismatic shape, located in the second straight section of the laryngoscope, at its distal end, immediately after the end of the curved section thereof.

16. The laryngoscope according to claim 1, characterized in that it incorporates a viewer (40) which is coupled to the proximal end of the laryngoscope, surrounding the four surfaces of the proximal area of the laryngoscope, including the housing of the battery, to maintain constant the distance between the eye of the person inserting the laryngoscope into the patient and a first lens (31) located at the proximal end of the laryngoscope.

17. The laryngoscope according to claim 1, characterized in that at its proximal end it incorporates a video camera (70) connected to a receiver.

18. The laryngoscope according to claim 17, characterized in that said connection between the video camera (70) and the receiver is a wireless connection.

19. The laryngoscope according to claim 1, characterized in that the laryngoscope is separated into two parts which can be coupled to one another, a first part (80) corresponding to a first straight section of the proximal area of the laryngoscope and comprising the housing of the battery, the first lens (31), the microcontroller (63), electric conductors and the viewer (40), and a second part corresponding to a second straight section and the curved section (90) of the laryngoscope to its distal area and comprising the lenses (32, 34, 35, 37) behind the first lens (31), the reflecting elements (33, 36), electric conductors and the lighting device.

20. The laryngoscope according to claim 19, characterized in that the coupling between said first part (80) and said second part (90) is carried out by means of flanges (81) arranged in the first part (80) which are housed in grooves (91) arranged in the second part (90).

21. The laryngoscope according to claim 19, characterized in that the coupling between the electric conductors of the first part (80) and of the second part (90) is carried out by means of jacks (82, 92).

22. The laryngoscope according to claim 1, characterized in that it has a second conduit (19) integrated in the body of the laryngoscope, used for inserting an endotracheal tube, which is separated from the viewing conduit (18) by the partition (13) and has an upper wall (14), continuation of the upper wall (11) of the viewing conduit (18), and a lower wall (15), continuation of the lower wall (12) of the viewing conduit (18), as well as a partially open side wall, opposite to the separating partition (13) for the separation with the viewing conduit (18).

23. The laryngoscope according to claim 22, characterized in that the side wall of the second conduit (19) is formed by three side walls for guiding the endotracheal tube, separated from one another, the first side wall being located at the distal end of the laryngoscope and covering the second straight section of the laryngoscope and the end of the curved section thereof, the second side wall, having a smaller length than the first side wall and being separated from it, is located immediately after the start of the curved section of the laryngoscope, and the third side wall, with a smaller size than the second side wall, is located approximately in the middle of the first straight section of the laryngoscope.

24. The laryngoscope according to claim 22, characterized in that the side wall of the second conduit (19) has a single side wall extending approximately from the middle of the first straight section of the laryngoscope to the end of the second straight section thereof.

25. The laryngoscope according to claim 22, characterized in that the second conduit (19) has no side wall or lower wall (15, 15'), it only has an upper wall (14").

26. The laryngoscope according to claim 1, characterized in that the optical elements are Fresnel prisms.

27. The laryngoscope according to claim 1, characterized in that it has a tab (16) at the distal end of the laryngoscope, extension of the upper wall (11) of the viewing conduit, and which is shifted towards the endotracheal conduit to lift the tissues which could fall thereon when it is being inserted inside the patient.

28. The laryngoscope according to claim 1, characterized in that it has a flange (17) or projection directed towards the inside of the endotracheal conduit (19), arranged in the side wall thereof and being wedge-shaped, directing the end of the endotracheal tube during its insertion towards the entrance of the trachea when it comes out of the endotracheal tube (19).

* * * * *